United States Patent [19]

Bewicke

[11] Patent Number: 5,770,207
[45] Date of Patent: Jun. 23, 1998

[54] DIETARY SUPPLEMENTS CONTAINING KAVA ROOT EXTRACT, PASSION FLOWER, CHAMOMILE FLOWERS, HOPS, AND SCHIZANDRA FRUIT

[75] Inventor: Calverly M. Bewicke, San Anselmo, Calif.

[73] Assignee: Natrol, Incorporated, Chatsworth, Calif.

[21] Appl. No.: 818,931

[22] Filed: Mar. 17, 1997

[51] Int. Cl.$^6$ .............................. A61K 35/78; A61K 9/48
[52] U.S. Cl. ........................................ 424/195.1; 424/451
[58] Field of Search .................................. 424/195.1, 451

[56] References Cited

U.S. PATENT DOCUMENTS 5,296,224  3/1994  Schwabe .............................. 424/195.1

OTHER PUBLICATIONS

Mowrey, The Scientific Validation of Herbal Medicine, Keats Publishing, Inc., New Canaan, CT, pp. 110, 163–166, 203–211 and 213–221, 1986.

Hoffmann, The Herbal Handbook, A User's Guide to Medicinal Herbalism, Healing Arts Press, Rochester, VT, pp. 72–73, 1988.

Reid, A Handbook of Chinese Healing Herbs, Shambhala Publications, Inc., Boston, MA, pp. 173–174, and 246–247, 1995.

The Merck Index, Tenth Ed., Merck & Co., Inc., Rahway, NJ p. 812, entry#5512, and p. 1299, entry#8915, 1983.

Munte et al, "Effects of Oxazepam and an Extract of Kava Roots (Piper methysticum) on Event–Related Potentials in a Word Recognition Task", *Neuropsychobiology* 1993:27, pp. 46–53.

Russell et al, "The Effects of Kava on Alerting and Speed of Access of Information from Long–term Memory", *Bulletin of the Psychonomic Society,* 25(4), pp. 236–237 (1987).

M. Schmidt, A Medicinal Plant from the South Seas, PTA heute, vol. 8, No. 5, May 1994.

*Primary Examiner*—David M. Naff
*Assistant Examiner*—Janet M. Kerr
*Attorney, Agent, or Firm*—Benman & Collins

[57] ABSTRACT

A novel dietary supplement composition is provided that serves as a general relaxant. The supplement comprises pharmaceutical grade Kava root extract and at least one additional relaxing herb selected from the group consisting of Passion Flower, Chamomile Flower, Hops, and Schizandra Fruit. The most preferred composition of the dietary supplement, in capsule form, comprises: (a) about 200 mg pharmaceutical grade Kava root extract; (b) about 50 mg Passion Flower; (c) about 50 mg Chamomile Flowers; (d) about 50 mg Hops; (e) about 50 mg Schizandra Fruit; (f) about 5 mg talc; and (g) about 5 mg magnesium stearate.

6 Claims, No Drawings

DIETARY SUPPLEMENTS CONTAINING KAVA ROOT EXTRACT, PASSION FLOWER, CHAMOMILE FLOWERS, HOPS, AND SCHIZANDRA FRUIT

BACKGROUND OF THE INVENTION

1. Field of the Invention

The present invention relates generally to dietary supplements, and, more particularly, to a special blend of Kava root extract and other relaxing herbs designed to produce general relaxation without involuntary drowsiness.

2. Description of Related Art

Throughout history, humans have ingested and otherwise consumed a wide variety of substances to effect relaxation, stress reduction, and an overall sense of well-being and tranquility. Examples of such substances include alcohol, marijuana, and prescription drugs such as valium. However, many such substances have significant undesirable side effects, including impairment of mental faculties, involuntary sleep, and the likelihood of user addiction. Thus, many relaxants are unsafe, especially for long-term usage.

One relaxant that does not typically exhibit any significant side effects is an extract from the Kava-kava root (hereinafter "Kava root", which consists of the dried rootstock and/or shoots of *Piper methysticum Forst* (Family: Piperaceae). The Kava root extract is known to induce general relaxation in humans when orally ingested. An aqueous macerate of the Kava root known as "kava" or "kawa" has been used on islands in the South Pacific in social gatherings and religious rituals for three thousand years.

In recent years, the Kava plant has been scientifically scrutinized, with many of its active constituents being identified. The psychoactive ingredients of the Kava root have been identified as kavalactones, also known as kavapyrones. A total of fifteen kavalactones have been identified to date, including kavain, dihydrokavain (a.k.a. marindinin), methysticin, dihydromethysticin, yangonin, and desmethoxyyangonin. These compounds are neutral, nitrogen-poor compounds that may be specifically referred to as substituted d-lactones and substituted a-pyrones. The lactone ring is substituted by a methoxy group in the C-4 position, and the differences in the compounds lie in the substitution by a styryl residue (e.g., yangonin, desmethyoxyyangonin, kavain, and methysticin) or by a phenyl residue (e.g., dihydrokavain and dihydromethysticin).

The particular kavalactones in a Kava root extract vary depending upon its origin. Further, the particular kavalactones present depend upon whether, in addition to rhizome parts, roots and stems of the plant are included in the extract. High quality extracts of the Kava root are sold based upon the total kavalactone content, rather than upon analysis of the individual lactones contained therein. The concentration ranges of total kavalactone levels in the Kava root extracts employed, e.g., in Germany are generally within the range of 30 to 55 wt %.

The Kava root extract lactones provide an anxiolytic effect, relieving nervous anxiety, tension, and restlessness, with their efficacy as a relaxant having been tested in clinical trials. The kavalactones also effect muscle relaxation. Studies have also shown that average single doses of Kava do not impair neurophysiological activity, as evidenced by such measuring indicia as recognition rates, event-related brain potentials, and driving ability (see, e.g., Münte et al, "Effects of Oxazepam and an Extract of Kava Roots (*Piper methysticum*) on Event-Related Potentials in a Word Recognition Task", *Neuropsychobiology* 1993:27, pp. 46–53 and Russell et al, "The Effect of Kava on Alerting and Speed of Access of Information from Long-term Memory", *Bulletin of the Psychonomic Society*, 25(4), pp. 236–37 (1987)). Further, kavalactones are non-addictive and do not induce involuntary sleep or effects of drunkenness.

Traditionally, Kava root is prepared for human consumption by pulverizing the plant material, mixing with water, and drinking the resulting liquid. Modern Kava root extracts are manufactured using ethanol as a solvent, as the kavalactones are readily soluble in ethanol. The extracted materials are in the form of a yellowish brown paste or powder, which is then tested to assure proper levels of kavalactones.

Today, Kava root extract is widely available in Germany and other European countries as an herbal supplement in the form of tablets, capsules, and dragees made of pharmaceutical grade extract. Ingestion of kavalactones in the form of drops is not desirable, given their bitter soapy taste. Typically, Kava root extract is commercially available in Europe with single doses containing 200–250 mg of extract with 30 wt % kavalactones, or about 60–75 mg kavalactones, and normal daily usage would be one to three capsules. Examples of available commercial extracts include the following trade designations, with the standardized milligrams of kavalactones in a dose indicated parenthetically if known: Antaresg®-120 (120 mg), Ardeydystin® forte (50 mg), Kava von ci (40 mg), Kavasedon® (25 mg per mL), Kavaspora® forte (50 mg), Kavatino® (25 mg), Laitin®-100 (70 mg), Kavain, Somnuvis®, Hewepsychon® duo (at least 24 mg per mL), Valeriana comp Hevertg®, and Cefakava® 150 (35 mg) (see M. Schmidt, "A Medicinal Plant from the South Seas", *PTA heute*, Vol. 8, No. 5, May 1994)).

Although ingestion of the Kava root extract does not typically exhibit the serious side effects of other common relaxants, it likewise should not be used in the case of pregnancy or lactation. A known possible side effect of prolonged ingestion of the Kava root extract is a temporary yellow discoloration of the skin and appendages, upon observance of which one should cease intake of the herb. Other rare side effects include allergic skin reactions, gastrointestinal complains such as nausea and diarrhea, accommodation disorders (disorders of the ability of the eye to adjust to see at various distances), dilations of the pupil, and disturbances of the oculometer equilibrium.

Given the long-established beneficial calming effect of the Kava root extract and its rare incidence of associated side effects, it would be desirable to provide the Kava root extract in a dietary supplement improved over that already commercially available. The dietary supplement should enhance the general relaxant qualities offered by the Kava root extract without introducing any harmful side effects. It should be inexpensively manufactured and comply with all applicable governmental regulations.

SUMMARY OF THE INVENTION

In accordance with the present invention, a dietary supplement is provided that comprises Kava root extract and at least one additional relaxing herb selected from the group consisting of Passion Flower, Chamomile Flowers, Hops, and Schizandra Fruit. The present supplement therefore enhances the general relaxation achieved from the consumption of Kava root extract alone.

DESCRIPTION OF THE PREFERRED EMBODIMENTS

The dietary supplement of the invention comprises Kava root extract and at least one additional relaxing herb selected from the group consisting of Passion Flower, Chamomile Flowers, Hops, and Schizandra Fruit. These additional relaxing herbs have been used as relaxants both traditionally and in modern herbal medical practice, such that the resulting dietary supplement essentially enhances the general relaxant qualities offered by the Kava root extract without introducing any harmful side effects. The dietary supplement composition is preferably put into capsules using known technology, such that the recommended daily dose for an adult would be one to three capsules.

The Kava root extract employed is a pharmaceutical grade extract that is commercially available, e.g., from Meggenburg, a German manufacturer. Pharmaceutical grade Kava root extract manufactured in Germany is standardized for kavalactone content of about 30 wt % and contains the full spectrum of lactones found in the Kava plant. The pharmaceutical grade extract must pass extensive safety and efficacy procedures. The extract employed in the practice of the invention preferably has a minimum kavalactone content of about 30 wt %.

In addition to Kava extract, the present dietary supplement contains at least one additional complementary relaxant herb to provide a calming and relaxing effect, among other benefits such as stress reduction, in addition to that effected by the Kava extract. The additional relaxant herb is selected from Passion Flower, Chamomile Flowers, Hops, and Schizandra Fruit, all of which are commercially available.

Preferably, a single dose or capsule of the present dietary supplement contains the following five relaxant herbs within the following ranges: (a) about 150 to 250 mg Kava root extract; (b) about 25 to 100 mg Passion Flower; (c) about 25 to 100 mg Chamomile Flowers; (d) about 25 to 100 mg Hops; and (e) about 25 to 100 mg Schizandra Fruit.

Passion Flower is a dry powdered herb deriving from *Passiflora incarnata*. Passion Flower has been traditionally used for it mild sedative effects; further, it advantageously has a pleasant taste and is surprisingly gentle. The plant contains a group of indole alkaloids and several flavonoids which are believed responsible for its sedative and analgesic effects. Both dried leaves and stems have been used to induce sleep, although the concentration of Passion Flower in the present dietary supplement is not enough to cause drowsiness.

Chamomile is a plant from the genus *Matricaria chemomilia*. Chamomile Flowers, in the form of a powdered herb, have been traditionally used in a tea for their sedative effect. It is now known that Chamomile Flowers contain a unique volatile oil, among other components, that account for their sedative effect.

Hops (*Humulus lupulus*) is a twisting vine of the mulberry family. Hops have traditionally been used in the form of a powdered herb for their calming and sedative properties. It has been shown that lupulin, which is a naturally-occurring constituent of hops, affects the central nervous system, causing a soothing and relaxing calm beginning about twenty minutes after ingestion.

Schizandra Fruit, which is a powered herb deriving from *Schizandra chinensis*, has been classified as an adaptogen because of its ability to balance and regulate many functions of the body. It is preferably included in this formula as a balancing agent to combat the widespread effects of stress.

In addition to the Kava root extract and the additional complementary relaxing herb, the present dietary supplement may include various additives such as other vitamins and minerals, as well as inert ingredients such as talc and magnesium stearate that are standard excipients in the manufacture of tablets and capsules. Preferably, talc and magnesium stearate are included in the present dietary supplement. Most preferably, the Astac Brand 400 USP talc powder and the vegetable grade of magnesium stearate are employed.

The most preferred composition of the present dietary supplement is as follows: (a) 200 mg Kava root extract (30% kavalactones); (b) 50 mg Passion Flowers powder; (c) 50 mg Chamomile Flowers powder; (d) 50 mg Hops powder; (e) 50 mg Schizandra powder; (f) 5 mg talc powder; and (g) 5 mg magnesium stearate.

Thus, there has been disclosed a dietary supplement comprising Kava root extract and at least one additional relaxing herb selected from the group consisting of Passion Flowers, Chamomile Flowers, Hops, and Schizandra. It will be readily apparent to those skilled in the art that various changes and modifications of an obvious nature may be made without departing from the spirit of the invention, and all such changes and modifications are considered to fall within the scope of the invention as defined by the appended claims.

What is claimed is:

1. A dietary supplement comprising, in capsule form, the following components:

a. about 150 to 250 mg pharmaceutical grade Kava root extract;

b. about 25 to 100 mg Passion Flower power;

c. about 25 to 100 mg Chamomile Flowers power;

d. about 25 to 100 mg Hops power; and e. about 25 to 100 mg Schizandra Fruit power.

2. The dietary supplement of claim 1 further comprising about 5 mg talc and about 5 mg magnesium stearate.

3. The dietary supplement of claim 1 wherein said Kava root extract contains at least about 30 wt % active kavalactones.

4. A dietary supplement comprising, in capsule form, the following components:

a. about 200 mg pharmaceutical grade Kava root extract;

b. about 50 mg Passion Flower power;

c. about 50 mg Chamomile Flowers power;

d. about 50 mg Hops power; and e. about 50 mg Schizandra Fruit power.

5. The dietary supplement of claim 4 further comprising about 5 mg talc and about 5 mg magnesium stearate.

6. The dietary supplement of claim 4 wherein said Kava root extract contains at least about 30 wt % active kavalactones.

* * * * *